United States Patent [19]

Rempfler et al.

[11] Patent Number: 4,629,813
[45] Date of Patent: Dec. 16, 1986

[54] HYDROXYPHENYLOXIME ETHERS

[75] Inventors: Hermann Rempfler, Ettingen, Switzerland; Georg Pissiotas, Lörrach, Fed. Rep. of Germany

[73] Assignee: Ciba-Geigy Corporation, Ardsley, N.Y.

[21] Appl. No.: 733,821

[22] Filed: May 14, 1985

[51] Int. Cl.$^4$ .................. C07C 131/00; C07C 103/29; C07C 101/00; C07D 211/72
[52] U.S. Cl. .................... 564/256; 546/300; 546/286; 560/35; 564/165; 558/391
[58] Field of Search ............... 546/300, 286; 564/256, 564/165; 560/35; 260/465 E; 558/391

[56] References Cited

U.S. PATENT DOCUMENTS 4,134,751  1/1979  Nishiyama et al. ............... 546/300

FOREIGN PATENT DOCUMENTS 0023891  8/1980  European Pat. Off. ............ 546/300

OTHER PUBLICATIONS

Noller, Textbook of Organic Chemistry, 3rd ed., W. B. Saunders Co., Philadelphia, 1966, pp. 204 & 375.

*Primary Examiner*—Henry H. Jiles
*Assistant Examiner*—Robert C. Whittenbaugh
*Attorney, Agent, or Firm*—Karl F. Jorda

[57] ABSTRACT

The present invention relates to a novel four-step process for the preparation of herbicidal and plant growth regulating 2-nitro-5-(2-pyridinyloxy)acetophenone oxime ether derivatives of formula I

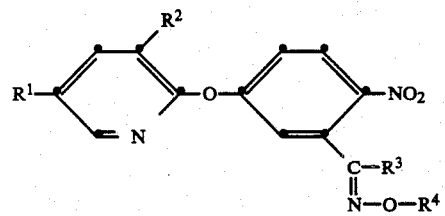

(I)

wherein
$R^1$ is hydrogen, cyano, halogen, nitro, $C_1$-$C_4$alkyl or $C_1$-$C_4$haloalkyl,
$R^2$ is hydrogen or halogen,
$R^3$ is $C_1$-$C_4$alkyl and
$R^4$ is $C_1$-$C_4$alkyl, $C_1$-$C_4$cyanoalkyl, $C_3$-$C_5$alkenyl, $C_3$-$C_5$haloalkenyl, $C_3$-$C_5$alkynyl, or $C_1$-$C_4$alkyl which is substituted by $C_1$-$C_4$alkoxy, halogen, $C_1$-$C_4$alkoxycarbonyl, $C_1$-$C_4$alkylaminocarbonyl or di($C_1$-$C_4$)alkylaminocarbonyl, which process comprises converting a phenol of formula II

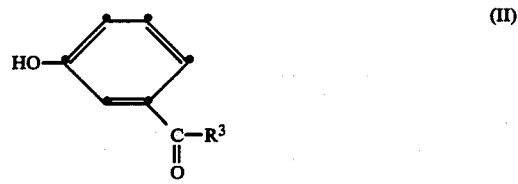

(II)

by reaction with a compound of formula

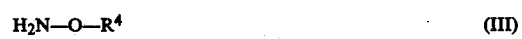

(III)

$$H_2N-O-R^4$$

into an oxime ether of formula IV

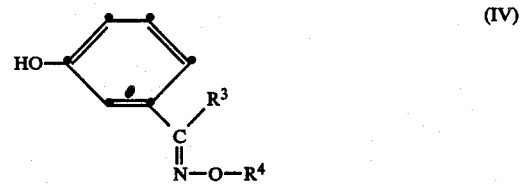

(IV)

in the presence of a base; reacting said oxime ether with a 2-halopyridine of formula V

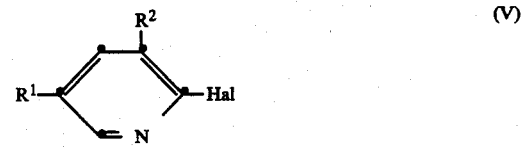

(V)

wherein Hal is chlorine or bromine, in the presence of an acid acceptor; and nitrating the resultant oxime ether of formula VI

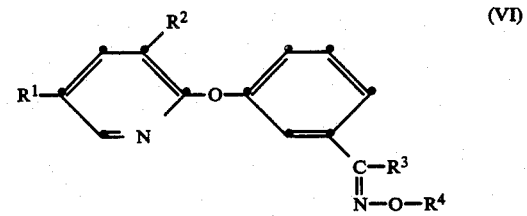

(VI)

with a nitrating agent.

3 Claims, No Drawings

HYDROXYPHENYLOXIME ETHERS

The present invention relates to a novel process for the preparation of derivatives of 2-nitro-5-(2-pyridinyloxy)acetophenone oxime ethers, and to novel intermediates which have been developed for said process.

2-Nitro-5-(2-pyridinyloxy)acetophenone oxime ether derivatives which can be prepared by the process of the present invention, the preparation and the use thereof are known for European patent specification No. 23 891. These compounds can be employed as selective herbicides or as plant growth regulators. With regard to product yield, the preparatory process referred to meets the demands of a process for the large-scale industrial preparation of compounds of formula I only insufficiently. Therefore a need exists for a preparatory process which provides the desired product in a higher yield. Surprisingly, the novel process of the present invention meets this demand substantially.

Accordingly, it is proposed in the present invention to prepare the 2-nitro-5-(2-pyridinyloxy)acetophenone oxime ether derivatives of formula I

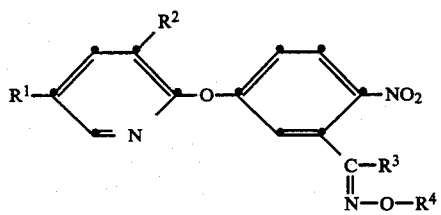

wherein
R$^1$ is hydrogen, cyano, halogen, nitro, C$_1$-C$_4$alkyl or C$_1$-C$_4$haloalkyl,
R$^2$ is hydrogen or halogen,
R$^3$ is C$_1$-C$_4$alkyl and
R$^4$ is C$_1$-C$_4$alkyl, C$_1$-C$_4$cyanoalkyl, C$_3$-C$_5$alkenyl, C$_3$-C$_5$haloalkenyl, C$_3$-C$_5$alkynyl, or C$_1$-C$_4$alkyl which is substituted by C$_1$-C$_4$alkoxy, halogen, C$_1$-C$_4$alkoxycarbonyl, C$_1$-C$_4$alkylaminocarbonyl or di(C$_1$-C$_4$)alkylaminocarbonyl,
by converting a phenol of formula II

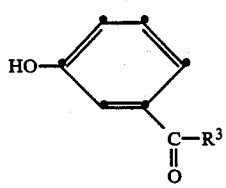

wherein R$^3$ is as defined for formula I, by reaction with a compound of formula III

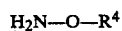

wherein R$^4$ is as defined for formula I, into an oxime ether of formula IV

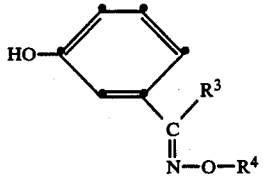

wherein R$^3$ and R$^4$ are as defined for formula I, in the presence of a base; reacting said oxime ether with a 2-halopyridine of formula V

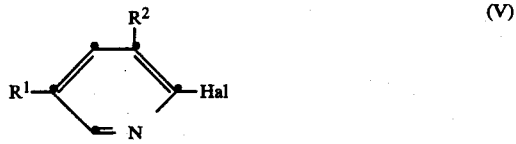

wherein R$^1$ and R$^2$ are as defined for formula I and Hal is chlorine or bromine, in the presence of an acid acceptor; and nitrating the resultant oxime ether of formula VI

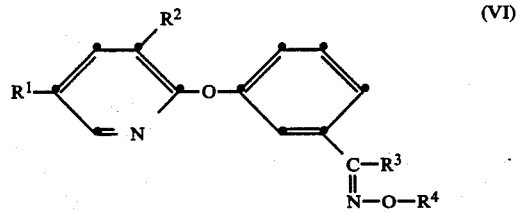

wherein R$^1$, R$^2$, R$^3$ and R$^4$ are as defined for formula I, with a nitrating agent.

In the above definitions, the generic terms indicated comprise for example the following specific individual substituents, the recitation of which constitutes no limitation of the invention:

alkyl: methyl, ethyl, n-propyl, isopropyl, n-butyl, isobutyl, sec-butyl and tert-butyl, preferably methyl and ethyl;

halogen: fluorine, chlorine, bromine and iodine, preferably fluorine and chlorine;

haloalkyl: fluoromethyl, difluoromethyl, trifluoromethyl, 2,2,2-trifluoroethyl, 2-fluoroethyl, 2-chloroethyl and 2,2,2-trichloroethyl, preferably trifluoroethyl and trifluoromethyl;

cyanoalkyl: cyanomethyl, cyanoethyl, cyanopropyl and cyanobutyl, preferably cyanomethyl;

alkenyl: allyl, 2-butenyl, 3-butenyl, methallyl, 2-methyl-2-butenyl, 3-methyl-2-butenyl, 3-pentenyl and 2-pentenyl, preferably allyl and methallyl;

alkynyl: propargyl, 2-butynyl, 3-butynyl, 2-pentynyl, 3-pentynyl and 4-pentynyl, preferably propargyl;

haloalkenyl: 4-chloro-2-butenyl, 4,4,4-trichloro-2-butenyl, 4,4,4-trifluoro-2-butenyl, 4-fluoro-2-butenyl.

Further substituted alkyl radicals falling within the definition of R$^4$ are for example: alkoxyalkyl such as methoxymethyl, ethoxymethyl, methoxyethyl, ethoxyethyl, 2,2-dimethoxyethyl, 2,2-diethoxyethyl or methoxypropyl, preferably methoxyethyl; the haloalkyl radicals recited above; alkoxycarbonylalkyl such as methoxycarbonylmethyl, 1-methoxycarbonylethyl, 2-methoxycarbonylethyl, ethoxycarbonylmethyl, 1-ethoxycarbonylethyl, 2-ethoxycarbonylethyl or isopropyloxycarbonylethyl; alkylaminocarbonylalkyl such as methylaminocarbonylmethyl, ethylaminocarbonylmethyl, 1-methylaminocarbonylethyl, 2-methylaminocarbonylethyl, 1-ethylaminocarbonylethyl or 2-ethylaminocarbonylethyl; dialkylaminocarbonylalkyl such as dimethylaminocarbonylmethyl, diethylaminocarbonylmethyl, 1-diethylaminocarbonylethyl, 2-diethylaminocarbonylethyl, 1-dimethylaminocarbonylethyl or 1-ethylmethylaminocarbonylethyl.

By the process of the present invention, preferably such compounds of formula I are prepared, wherein $R^1$ is fluorine, chlorine, bromine or trifluoromethyl, $R^2$ is hydrogen, fluorine, chlorine or bromine, $R^3$ is methyl and $R^4$ is $C_1$–$C_3$alkyl or $C_1$–$C_3$alkyl which is substituted by cyano, $C_1$–$C_3$alkoxycarbonyl or $C_1$–$C_3$alkoxy.

The compounds of formula I, as also the intermediates of formulae IV and VI, may be obtained, in the oxime ether function, in the form of E and Z structural isomers. Normally, mixtures of the E and Z forms will be obtained. As a result of the steric conditions of the reaction partners, the respective ratio of E to Z may vary greatly. The separation of mixtures of the E and Z structural isomers can be effected by methods of separation well known to the person skilled in the art. Unless otherwise specifically stated in the present specification, the compounds of formulae I, IV and VI will be understood as meaning those mixtures of E and Z structural isomers which are obtained by the reaction of the present invention. Wherever individual structural isomers are meant, this is specifically stated.

In the first reaction step (II+III→IV), the carbonyl group is converted in a manner known per se into the oxime ether group, in the presence of a base. Both the use of a solvent and the addition of a base to the reaction mixture are advantageous. Suitable solvents are: alcohols such as methanol, ethanol or isopropanol; chlorinated hydrocarbons such as methylene chloride, chloroform, carbon tetrachloride, trichloroethane, tetrachloroethane, chlorobenzene or dichlorobenzene; nitriles such as acetonitrile or propionitrile; amides such as dimethylformamide or N,N-dimethylacetamide; esters such as ethyl acetate; or dimethylsulfoxide. Both inorganic and organic bases can be employed, e.g. alkali metal hydroxides such as lithium hydroxide, sodium hydroxide or potassium hydroxide; carbonates such as sodium carbonate, potassium carbonate, magnesium carbonate or calcium carbonate; alcoholates such as potassium tert-butylate, sodium methylate, sodium ethylate, potassium ethylate or sodium isopropylate; or amines such as trimethylamine, triethylamine, pyridine, quinuclidine, 1,4-diazabicyclo[2.2.2]octane, 1,8-diazabicyclo[5.4.0]undec-7-ene or 1,5-diazabicyclo[4.3.0]non-5-ene. The reaction temperatures for the first reaction step (II+III→IV) are generally in the range from 0° C. to +120° C., preferably from +10° C. to +50° C. Preferred reaction conditions for the first step (II+III→IV) are: temperatures in the range from +10° C. to 50° C., the use of sodium hydroxide as acid acceptor and of ethanol as solvent.

In the second step of the process of this invention, the ether coupling (IV+V→VI) is carried out in the presence of a base, advantageously choosing an inert solvent as reaction medium. The reaction temperatures for the second reaction step (IV+V→VI) are generally in the range from −20° C. to +120° C., preferably from 0° C. to +60° C.

Suitable acid acceptors are: alcoholates such as potassium tert-butylate, sodium ethylate, potassium ethylate, sodium methylate or sodium isopropylate; hydroxides such as lithium hydroxide, sodium hydroxide or potassium hydroxide; oxides such as magnesium oxide or calcium oxide; or carbonates such as sodium carbonate, potassium carbonate, magnesium carbonate or calcium carbonate. If the reaction (IV+V→VI) is carried out in a solvent, a polar organic solvent is preferably used. Examples of such solvents are: ketones such as acetone, 2-butanone, cyclohexanone or methyl isobutyl ketone; nitriles such as acetonitrile or propionitrile; amides such as dimethylformamide or N,N-dimethylacetamide; and dimethylsulfoxide. Preferred reaction conditions are: temperatures in the range from 0° C. to +60° C., and the presence of sodium hydroxide as base and of dimethylsulfoxide as solvent.

In the third reaction step, the intermediate of formula VI is nitrated with a nitrating reagent to give a compound of the formula I. Suitable customary nitrating agents are: nitric acid, nitric acid/sulfuric acid mixtures, nitric anhydride ($N_2O_5$) or mixtures of nitric acid with sulfuric acid and oleum. The nitration reaction can be carried out without a solvent or, advantageously, in an inert organic solvent. Suitable solvents are: chlorinated hydrocarbons such as methylene chloride, chloroform, carbon tetrachloride, 1,2-dichloroethane, trichloroethane, tetrachloroethane, chlorobenzene or dichlorobenzene. The reaction temperatures for the third step are generally in the range from −20° C. to +50° C., preferably from −10° C. to +30° C. In a preferred embodiment, the third step (VI→I) is carried out at a temperature in the range from −10° C. to +30° C. in 1,2-dichloroethane, in which step 100% nitric acid in the presence of sulfuric acid and oleum is employed as nitrating agent.

In a preferred embodiment of the process of the present invention, the compounds of formula I are obtained by reacting a phenol of formula II with a compound of formula III, at a temperature in the range from +10° C. to +50° C. and in the presence of potassium hydroxide in ethanol; etherifying the resultant oxime ether of formula IV, at a temperature in the range from 0° C. to +60° C. and in the presence of sodium hydroxide in dimethylsulfoxide, with a 2-halopyridine of formula V; and nitrating the resultant oxime ether of formula VI, at a temperature in the range from 0° C. to +30° C., in 1,2-dichloroethane, with a nitric acid/sulfuric acid/oleum mixture.

This preferred process is particularly suitable for preparing such compounds of formula I, wherein $R^1$ is fluorine, chlorine, bromine or trifluoromethyl, $R^2$ is hydrogen, fluorine, chlorine or bromine, $R^3$ is methyl and $R^4$ is $C_1$–$C_3$alkyl or $C_1$–$C_3$alkyl which is substituted by cyano, $C_1$–$C_3$alkoxycarbonyl or $C_1$–$C_3$alkoxy.

The starting materials of formulae II, III and V are known and can be prepared by processes known in the literature. Some of these materials are commercially available.

The intermediates of formulae IV and VI are novel. They have been specially developed and prepared for carrying out the process of this invention. Accordingly, the compounds of formulae IV and VI constitute an object of the invention.

The following Examples serve to illustrate in more detail the individual steps of the process of this invention. The subsequent tables showing intermediates and final products of formulae I, IV and VI illustrate the broad applicability of the novel process.

EXAMPLE 1

3-Hydroxyacetophenone oxime ethyl ether 9.7 g (0.1 mol) of ethoxyamine hydrochloride and 10 ml of a 30% aqueous solution of sodium hydroxide are added to a solution of 13.6 g (0.1 mol) of 3-hydroxyacetophenone in 200 ml of ethanol. The reaction mixture is kept for 2 hours at a temperature in the range from 20° C. to 25° C. and, after addition of 1 ml of glacial acetic acid, is heated for 2 hours to reflux. The solution is concentrated by evaporation and the residue is taken up in a mixture of diethyl ether and water. The organic phase is separated, washed with a 10% solution of sodium bicarbonate, dried over sodium sulfate and concentrated by evaporation. The residue is purified by chromatography over sililca gel eluted with a mixture of ethyl acetate/hexane (1:2), affording 14.9 g (83% of theory) of 3-hydroxyacetophenone oxime ethyl ether, $n_D^{25}$ 1.5502.

EXAMPLE 2

3-(3-Chloro-5-trifluoromethylpyridin-2-yloxy)acetophenone oxime ethyl ether 5 ml of a 20% aqueous solution of sodium hydroxide are added at a temperature of 20° C. to a solution of 9.0 g (0.05 mol) of 3-hydroxyacetophenone oxime ethyl ether in 50 ml of dimethylsulfoxide. 10.8 g (0.05 mol) of 2,3-dichloro-5-trifluoromethylpyridine are then added dropwise to the reaction mixture, whereupon the temperature of the mixture increases to 27° C. After a reaction time of 2 hours, the reaction mixture is taken up in ice water and the solution is extracted with ethyl acetate. The combined organic phases are washed with water, dried over sodium sulfate and concentrated by evaporation, affording 17.7 g (99% of theory) of 3-(3-chloro-5-trifluoromethylpyridin-2-yloxy)acetophenone oxime ethyl ether, $n_D^{25}$ 1.5340.

EXAMPLE 3

2-Nitro-5-(3-chloro-5-trifluoromethylpyridin-2-yloxy)acetophenone oxime ethyl ether 10 ml of 98% sulfuric acid and 1 ml of 25% oleum are added dropwise at −5° C. to a solution of 5.2 g (0.015 mol) of 3-(3-chloro-5-trifluoromethylpyridin-2-yloxy)acetophenone oxime ethyl ether in 50 ml of 1,2-dichloroethane. At 0° C., a solution of 2.5 ml of 100% nitric acid in 3 ml of 98% sulfuric acid is added dropwise. The reaction mixture is stirred for 7 hours at room temperature and then ice and ether are added. The ethereal phase is washed with water and with a saturated solution of sodium bicarbonate, dried over sodium sulfate and concentrated by evaporation. Purification by chromamtography over silica gel eluted with ethyl acetate/hexane (1:3) affords 3.5 g of pure 2-nitro-5-(3-chloro-5-trifluoromethylpyridin-2-yloxy)acetophenone oxime ethyl ether, $n_D^{30}$ 1.5418.

The intermediates and final products listed in Tables 1 to 3 are obtained in analogous manner.

TABLE 1

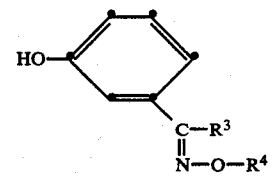

| Compound | $R^3$ | $R^4$ | Physical data |
|---|---|---|---|
| 1.01 | $CH_3$ | $C_2H_5$ | $n_D^{25}$ 1.5502 |
| 1.02 | $CH_3$ | $CH_3$ | |
| 1.03 | $CH_3$ | $-CH_2-CH=CH_2$ | $n_D^{25}$ 1.5616 |
| 1.04 | $CH_3$ | $-CH_2-CH_2-OCH_3$ | |
| 1.05 | $CH_3$ | $-CH_2-CH_2Cl$ | |
| 1.06 | $CH_3$ | $-CH_2-CH=CHCl$ | |
| 1.07 | $CH_3$ | $-CH_2-COOCH_3$ | |
| 1.08 | $CH_3$ | $-CH_2-COOC_2H_5$ | |
| 1.09 | $CH_3$ | $-CH(CH_3)-COOCH_3$ | |
| 1.10 | $C_2H_5$ | $C_2H_5$ | |
| 1.11 | $C_3H_7-n$ | $C_2H_5$ | |

TABLE 2

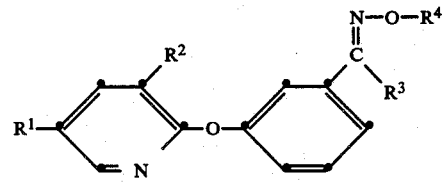

| Compound | $R^1$ | $R^2$ | $R^3$ | $R^4$ | Physical data |
|---|---|---|---|---|---|
| 2.01 | Cl | Cl | $CH_3$ | $-CH_2-COOC_2H_5$ | |
| 2.02 | Cl | Cl | $CH_3$ | $-C_2H_5$ | |
| 2.03 | Cl | Cl | $CH_3$ | $-CH(CH_3)-COOCH_3$ | |
| 2.04 | Cl | F | $CH_3$ | $-CH_2-CN$ | |
| 2.05 | Cl | F | $CH_3$ | $-CH_2-COOCH_3$ | |
| 2.06 | $CF_3$ | Cl | $CH_3$ | $-CH_2-COOC_2H_5$ | $n_D^{24}$ 1.5300 |
| 2.07 | $CF_3$ | Cl | $CH_3$ | $-CH_2-CON(CH_3)_2$ | |
| 2.08 | $CF_3$ | Cl | $CH_3$ | $-CH_2-CN$ | |
| 2.09 | $CF_3$ | Cl | $CH_3$ | $-CH_2-CH_2-OCH_3$ | |
| 2.10 | $CF_3$ | Cl | $CH_3$ | $-CH_2-CH_2-OC_2H_5$ | |
| 2.11 | $CF_3$ | Cl | $CH_3$ | $-CH_2-CH=CH-CH_2Cl$ | |
| 2.12 | $CF_3$ | Cl | $CH_3$ | $-CH_2-CH_2-COOC_2H_5$ | |
| 2.13 | $CF_3$ | Cl | $CH_3$ | $-CH_2-CONHCH_3$ | |
| 2.14 | $CF_3$ | Cl | $CH_3$ | $-CH(CH_3)-COOCH_3$ | |
| 2.15 | $CF_3$ | Cl | $CH_3$ | $-CH(CH_3)-CON(CH_3)_2$ | |
| 2.16 | $CF_3$ | H | $CH_3$ | $-CH_2-COOCH_3$ | |
| 2.17 | $CF_3$ | H | $CH_3$ | $-CH_2-CN$ | |
| 2.18 | $CF_3$ | H | $CH_3$ | $-C_2H_5$ | |

TABLE 2-continued

Structure: pyridine ring with R¹, R² substituents connected via O to phenyl ring with C(=N-O-R⁴)R³ group

| Compound | R¹ | R² | R³ | R⁴ | Physical data |
|---|---|---|---|---|---|
| 2.19 | $CF_3$ | H | $CH_3$ | $-CH_3$ | |
| 2.20 | $CF_3$ | F | $CH_3$ | $-CH_2-COOC_2H_5$ | |
| 2.21 | $CF_3$ | Cl | $C_2H_5$ | $-CH_2-COOC_2H_5$ | |
| 2.22 | $CF_3$ | Cl | $C_3H_7-n$ | $-CH_2-COOC_2H_5$ | |
| 2.23 | $CF_3$ | Cl | $C_4H_9-n$ | $-CH_2-COOC_2H_5$ | |
| 2.24 | $CF_3$ | Cl | $CH_3$ | $CH_3$ | |
| 2.25 | $CF_3$ | Cl | $CH_3$ | $-CH_2-CH=CH_2$ | $n_D^{30}$ 1.5385 |
| 2.26 | $CF_3$ | Cl | $CH_3$ | $-CH_2-CH=CHCl$ | $n_D^{25}$ 1.5619 |
| 2.27 | $CF_3$ | Cl | $CH_3$ | $-CH_2-COOCH_3$ | |
| 2.28 | $CF_3$ | Cl | $C_2H_5$ | $C_2H_5$ | |
| 2.29 | $CF_3$ | Cl | $CH_3$ | $C_2H_5$ | $n_D^{25}$ 1.5340 |
| 2.30 | $CF_3$ | Cl | $C_3H_7-n$ | $C_2H_5$ | |
| 2.31 | Cl | F | $CH_3$ | $-CH_2-CH=CHCl$ | |
| 2.32 | $CF_3$ | F | $CH_3$ | $-CH_2-CH_2-OCH_3$ | |

TABLE 3

Structure: pyridine ring with R¹, R² substituents connected via O to phenyl ring bearing $-NO_2$ and C(=N-O-R⁴)R³ group

| Compound | R¹ | R² | R³ | R⁴ | Physical data |
|---|---|---|---|---|---|
| 3.01 | Cl | Cl | $CH_3$ | $-CH_2-COOC_2H_5$ | |
| 3.02 | Cl | Cl | $CH_3$ | $-C_2H_5$ | |
| 3.03 | Cl | Cl | $CH_3$ | $-CH(CH_3)-COOCH_3$ | |
| 3.04 | Cl | F | $CH_3$ | $-CH_2-CN$ | |
| 3.05 | Cl | F | $CH_3$ | $-CH_2-COOCH_3$ | |
| 3.06 | $CF_3$ | Cl | $CH_3$ | $-CH_2-COOC_2H_5$ | $n_D^{25}$ 1.5350 |
| 3.07 | $CF_3$ | Cl | $CH_3$ | $-CH_2-CON(CH_3)_2$ | |
| 3.08 | $CF_3$ | Cl | $CH_3$ | $-CH_2-CN$ | |
| 3.09 | $CF_3$ | Cl | $CH_3$ | $-CH_2-CH_2-OCH_3$ | |
| 3.10 | $CF_3$ | Cl | $CH_3$ | $-CH_2-CH_2-OC_2H_5$ | |
| 3.11 | $CF_3$ | Cl | $CH_3$ | $-CH_2-CH=CH-CH_2Cl$ | |
| 3.12 | $CF_3$ | Cl | $CH_3$ | $-CH_2-CH_2-COOC_2H_5$ | |
| 3.13 | $CF_3$ | Cl | $CH_3$ | $-CH_2-CONHCH_3$ | |
| 3.14 | $CF_3$ | Cl | $CH_3$ | $-CH(CH_3)-COOCH_3$ | $n_D^{35}$ 1.5302 |
| 3.15 | $CF_3$ | Cl | $CH_3$ | $-CH(CH_3)-CON(CH_3)_2$ | |
| 3.16 | $CF_3$ | H | $CH_3$ | $-CH_2-COOCH_3$ | |
| 3.17 | $CF_3$ | H | $CH_3$ | $-CH_2-CN$ | |
| 3.18 | $CF_3$ | H | $CH_3$ | $-C_2H_5$ | |
| 3.19 | $CF_3$ | H | $CH_3$ | $-CH_3$ | |
| 3.20 | $CF_3$ | F | $CH_3$ | $-CH_2-COOC_2H_5$ | |
| 3.21 | $CF_3$ | Cl | $C_2H_5$ | $-CH_2-COOC_2H_5$ | |
| 3.22 | $CF_3$ | Cl | $C_3H_7-n$ | $-CH_2-COOC_2H_5$ | |
| 3.23 | $CF_3$ | Cl | $C_4H_9-n$ | $-CH_2-COOC_2H_5$ | |
| 3.24 | $CF_3$ | Cl | $CH_3$ | $CH_3$ | |
| 3.25 | $CF_3$ | Cl | $CH_3$ | $-CH_2-CH=CH_2$ | |
| 3.26 | $CF_3$ | Cl | $CH_3$ | $-CH_2-CH=CHCl$ | |
| 3.27 | $CF_3$ | Cl | $CH_3$ | $-CH_2-COOCH_3$ | |
| 3.28 | $CF_3$ | Cl | $C_2H_5$ | $C_2H_5$ | |
| 3.29 | $CF_3$ | Cl | $CH_3$ | $C_2H_5$ | $n_D^{30}$ 1.5418 |
| 3.30 | $CF_3$ | Cl | $C_3H_7-n$ | $C_2H_5$ | |
| 3.31 | Cl | F | $CH_3$ | $-CH_2-CH=CHCl$ | |
| 3.32 | $CF_3$ | F | $CH_3$ | $-CH_2-CH_2-OCH_3$ | |

What we claim is:
1. An oxime ether of formula IV

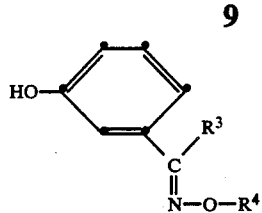

wherein
R³ is C₁–C₄alkyl and (IV) R⁴ is C₁–C₄alkyl, C₁–C₄cyanoalkyl, C₃–C₅alkenyl, C₃–C₅-haloalkenyl, C₃–C₅alkynyl, or C₁–C₄alkyl which is substituted by C₁–C₄alkoxy, halogen, C₁–C₄alkoxycarbonyl, C₁–C₄alkylaminocarbonyl or di(C₁–C₄)alkylaminocarbonyl.

2. An oxime according to claim 1 which is 3-hydroxyacetophenone oxime ethyl ether.

3. An oxime according to claim 1 which is 3-hydroxyacetophenone oxime allyl ether.

* * * * *